United States Patent
Muldner

(10) Patent No.: US 6,911,031 B2
(45) Date of Patent: Jun. 28, 2005

(54) SINGLE-HAND OPERABLE MICRODERMABRASION DEVICE

(76) Inventor: Janelle Marie Muldner, 100 North Arlington Ave., Reno, NV (US) 89501

( * ) Notice: Subject to any disclaimer, the term of this patent is extended or adjusted under 35 U.S.C. 154(b) by 0 days.

(21) Appl. No.: 09/960,139

(22) Filed: Sep. 24, 2001

(65) Prior Publication Data
US 2003/0060834 A1 Mar. 27, 2003

(51) Int. Cl.[7] .............................................. A61B 17/50
(52) U.S. Cl. ...................................................... 606/131
(58) Field of Search .............................. 606/131, 132, 606/133, 43, 85, 180; 604/289, 290, 313, 315; 451/48, 359, 353, 289, 548

(56) References Cited

U.S. PATENT DOCUMENTS

| | | | | |
|---|---|---|---|---|
| 1,919,571 A | * | 7/1933 | Pinkston | 451/359 |
| 2,701,559 A | * | 2/1955 | Cooper | 600/569 |
| 2,712,823 A | * | 7/1955 | Kurtin | 606/131 |
| 2,714,788 A | * | 8/1955 | Giovanna | 606/131 |
| 2,867,214 A | * | 1/1959 | Wilson | 606/131 |
| 2,881,763 A | * | 4/1959 | Robbins | 606/131 |
| 2,921,585 A | * | 1/1960 | Schumann | 606/131 |
| 3,468,079 A | * | 9/1969 | Kaufman | 606/131 |
| 3,964,212 A | * | 6/1976 | Karden | 451/358 |
| 4,378,804 A | * | 4/1983 | Cortese, Jr. | 606/131 |
| 4,891,915 A | * | 1/1990 | Yasuda | 51/170 T |
| 4,957,747 A | * | 9/1990 | Stiefel | 424/691 |
| 5,012,797 A | * | 5/1991 | Liang et al. | 601/2 |
| 5,037,431 A | * | 8/1991 | Summers et al. | 606/131 |
| 5,037,432 A | * | 8/1991 | Molinari | 606/131 |
| 5,100,412 A | * | 3/1992 | Rosso | 606/131 |
| 5,125,190 A | * | 6/1992 | Buser et al. | 51/273 |
| 5,207,234 A | * | 5/1993 | Rosso | 128/898 |
| 5,377,699 A | * | 1/1995 | Varnum | 606/131 |
| 5,545,082 A | * | 8/1996 | Courson et al. | 451/456 |
| 5,791,979 A | * | 8/1998 | Duncan et al. | 451/456 |
| 5,800,446 A | * | 9/1998 | Banuchi | 606/131 |
| 5,810,842 A | * | 9/1998 | Di Fiore et al. | 606/131 |
| 5,971,999 A | * | 10/1999 | Naldoni | 606/131 |
| 5,993,305 A | * | 11/1999 | Chu | 451/357 |
| 6,042,552 A | * | 3/2000 | Cornier | 600/562 |
| 6,139,553 A | * | 10/2000 | Dotan | 606/131 |
| 6,235,039 B1 | * | 5/2001 | Parkin et al. | 606/131 |
| 6,241,739 B1 | * | 6/2001 | Waldron | 606/131 |

* cited by examiner

*Primary Examiner*—Eduardo C. Robert
(74) *Attorney, Agent, or Firm*—Sierra Patent Group, Ltd.

(57) ABSTRACT

A microdermabrasion device is disclosed for removing cells from a patient's skin. The device includes a partial vacuum channel for drawing skin into intimate contact with an abrasive surface and drawing away removed skin cells.

3 Claims, 4 Drawing Sheets

SINGLE-HAND OPERABLE MICRODERMABRASION DEVICE

BACKGROUND

1. Field of the Disclosure

The disclosure relates generally to microdermabrasion devices for removing dead dry surface portions of tissue.

2. The Prior Art

BACKGROUND

Microdermabrasion is a process for removing undesirable outer layers of the skin, resulting in a cleaner skin and enhanced skin tone. Problem areas of the skin, such as acne scars, age spots, and sun damaged skin may be removed to improve the patient's appearance.

One current trend is to utilize additional surface treatments to enhance the abrasion process, such as chemicals or additional abrasives. However, such treatments are often expensive, require additional precautions, and often leave undesirable residue that must be properly disposed after treatment. Such additional treatments also limit the ability to treat the patient to an office setting or other controlled environment.

BRIEF DESCRIPTION OF THE DRAWING FIGURES

DETAILED DESCRIPTION

Figure 1:
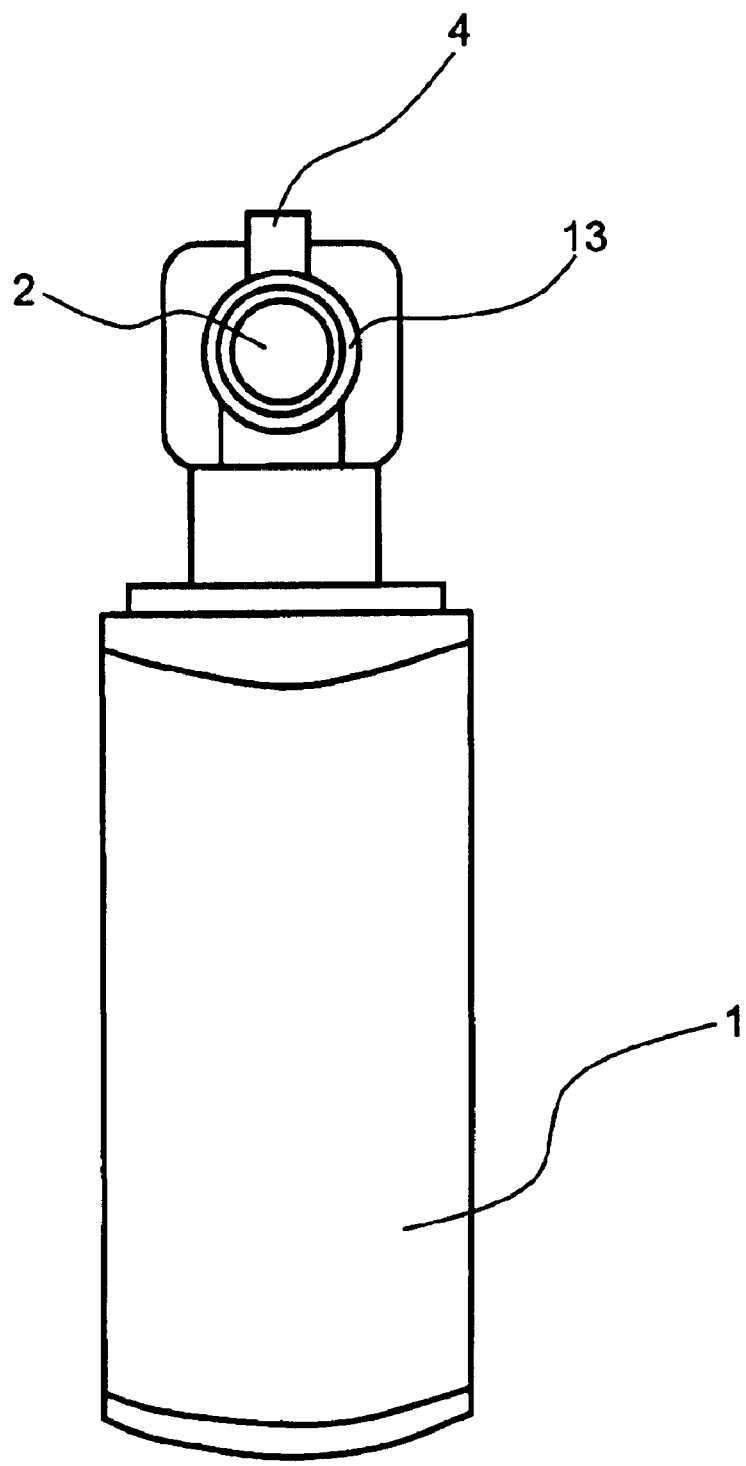
FIG. 1 is a front view of a microdermabrasion device configured in accordance with the teachings of this disclosure.

Persons of ordinary skill in the art will realize that the following description is illustrative only and not in any way limiting. Other modifications and improvements will readily suggest themselves to such skilled persons having the benefit of this disclosure. In the following description, like reference numerals refer to like elements throughout.

FIG. 1 is a front view of a microdermabrasion device configured in accordance with the teachings of this disclosure. The device includes a body 1 that is coupled to a partial vacuum housing 4 through motor housing 10 having a motor. The body 1 may be formed of materials known in the art, such as injection molded plastics and the like. The body may contain a conventional power source (not shown), such as a battery, for powering the device.

FIG. 1 also shows a front view of the outer abrading surface of a disposable abrading attachment 2 disposed within a removable housing 13, in a manner more fully disclosed below. In preferred embodiments, the surface of the abrading attachment 2 may have a layer of abrasive particles disposed thereon. In a further preferred embodiment, the abrading particles may be embedded in a disposable surface that may be removably affixed to the abrading attachment, such as through adhesives known in the art.

Figure 2:
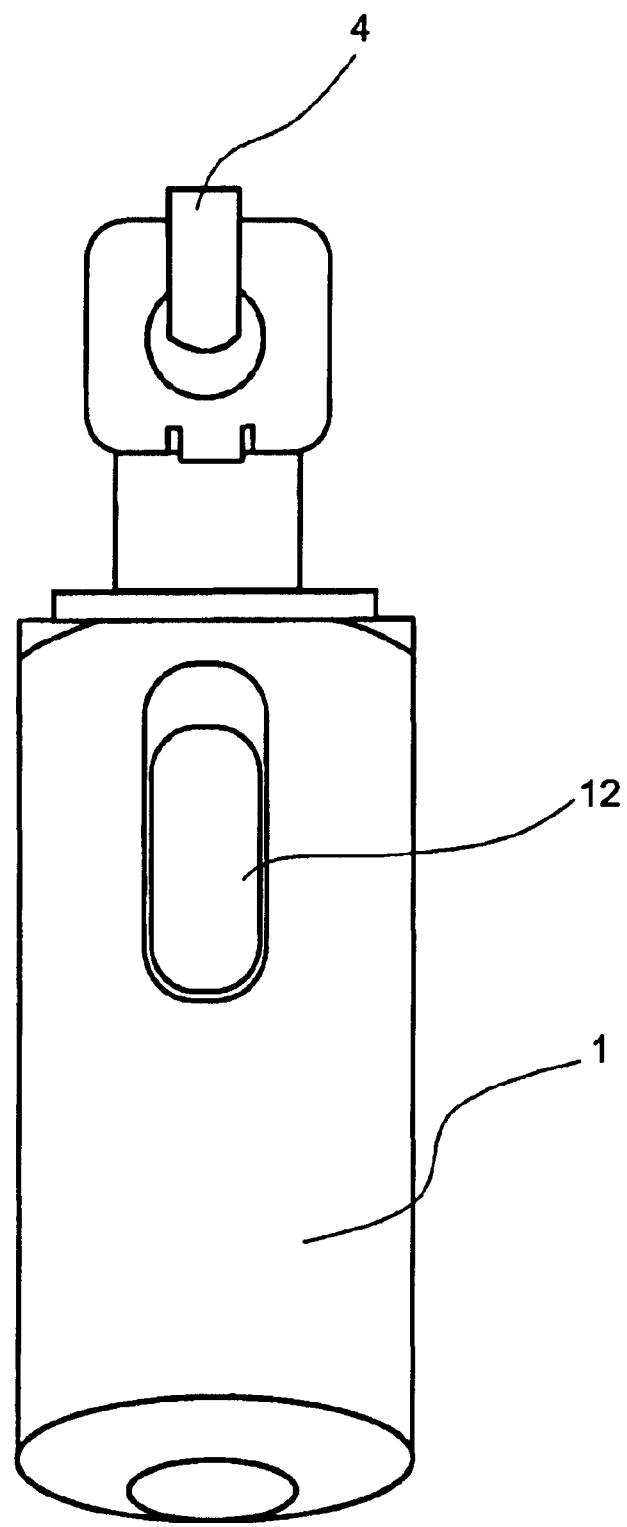
FIG. 2 shows a rear view of a microdermabrasion device.

FIG. 2 shows a rear view of a microdermabrasion device including a power switch 12 configured using techniques known in the art for connecting and disconnecting power to the device.

Figure 3:
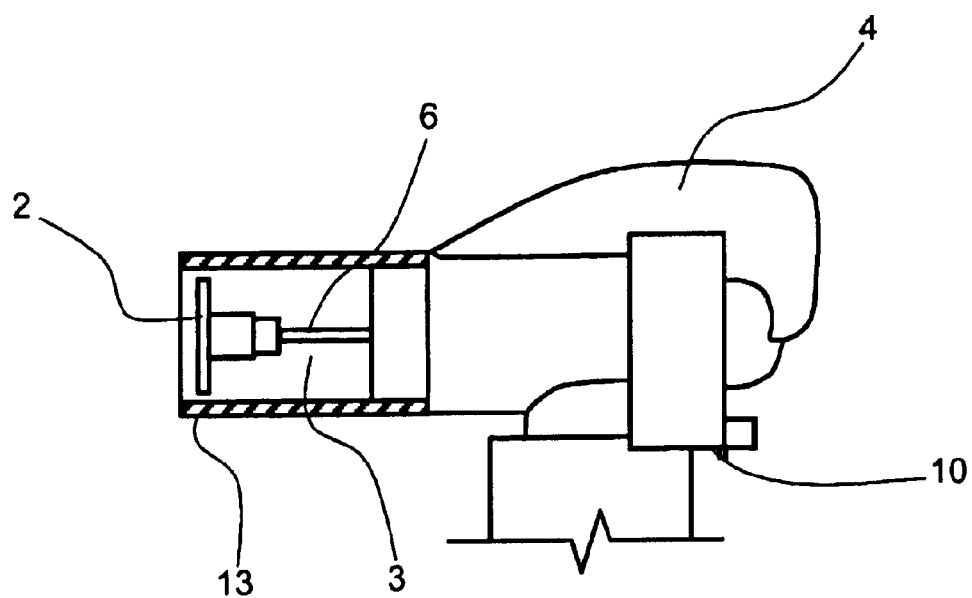
FIG. 3 is partial cutaway view of the housing showing the configuration of the abrading attachment.

FIG. 3 is partial cutaway view of the housing showing the configuration of the abrading attachment. FIG. 3 shows that the abrading attachment 2 may be coupled to the motor housing 10 through an extension arm 6. It is contemplated that the abrading attachment 2 may be releasably attached to the arm 6 as will more fully shown below.

FIG. 3 also shows that the abrading attachment 2 may be disposed in a partial vacuum channel as defined in the interior of a detachable tip 13.

Figure 4:
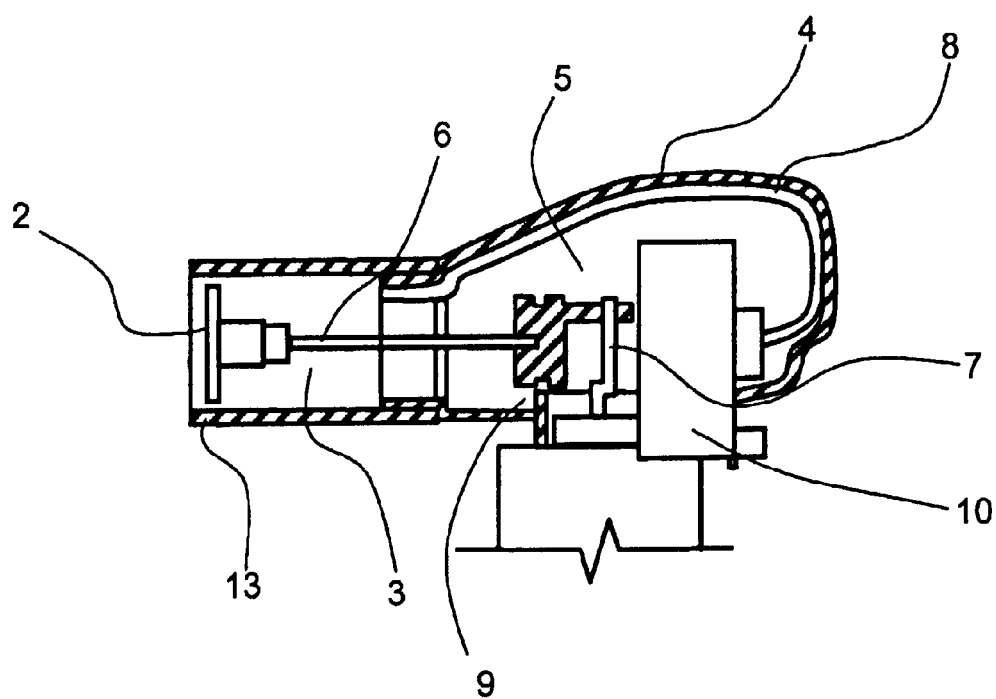
FIG. 4 is a more detailed cutaway diagram of the partial vacuum housing.

FIG. 4 is a more detailed cutaway diagram of the partial vacuum housing 4. FIG. 4 shows a suction channel 8 disposed along the interior wall of the housing 4. The channel 8 is coupled to the motor of motor housing 10 configured to created a vacuum flow in the channel 8 using conventional means.

As can be seen from FIG. 4, the suction channel 8 preferably terminates within the tip 13 proximate to and behind the abrading attachment to create a partial vacuum at the terminus of the channel. In this manner, the suction channel 8 creates a partial vacuum to remove abraded skin cells from the interior 3 of the tip 13.

As will now be appreciated by those of ordinary skill in the art, by so locating the terminus of the channel 8, a partial vacuum may be created in a manner to both draw the skin into intimate contact with the abrading attachment 2 in a manner suitable for treatment, and remove waste material from the interior 3. Additionally, the power requirement to create a partial vacuum is lower than the requirement to create a full vacuum in the interior 3 of the tip 13.

FIG. 4 also shows that the tip 13 may be removably attached to the housing 4 using techniques known in the art, such a being frictionally coupled as shown in the cutaway illustration of FIG. 4.

FIG. 4 also shows that the inner end of arm 6 is coupled to the motor housing 10 through conventional linkage 5 so as to provide an oscillating movement to the abrading attachment 2, thereby abrading the surface of skin brought into intimate contact with the surface of attachment 2. In one aspect, the motor in motor housing 10 moves an actuating member 7 in a direction traverse to the length of arm 6, oscillating linkage 5 about a pivot point 9, thereby imparting a oscillatory action to the surface of the abrading attachment 2.

Figure 5:
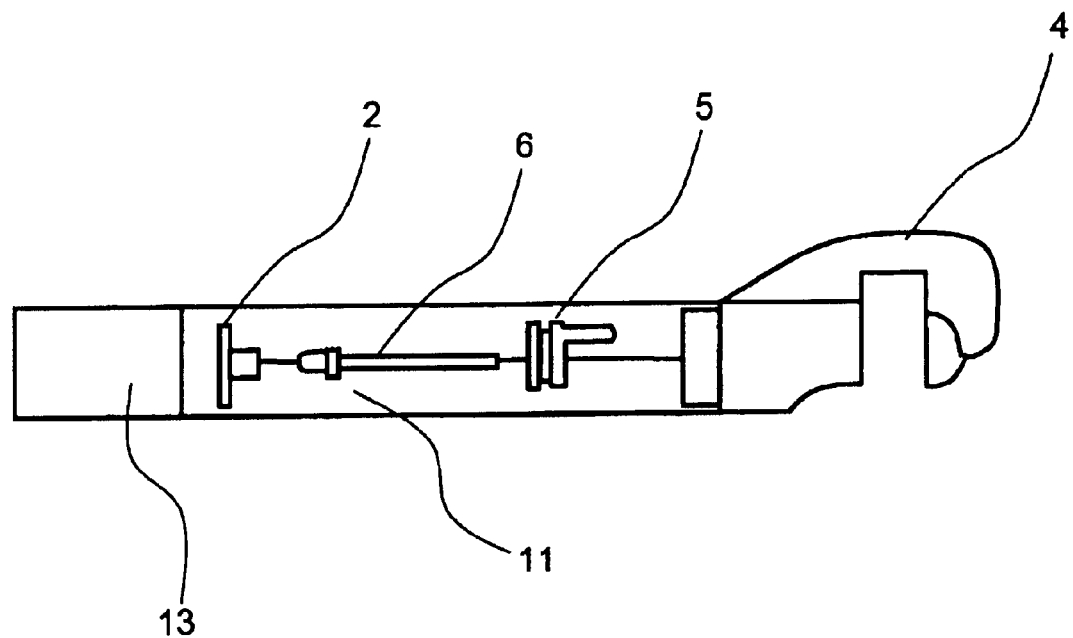
FIG. 5 is a exploded view of a preferred aspect of attaching a abrading surface to the device.

FIG. 5 is a exploded view of a preferred aspect of attaching a abrading surface to the device. FIG. 5 shows that the arm 6 may include a connecting tip 11 formed in the end thereof for allowing the abrading attachment to be removably attached. The tip 11 may be configured as shown to be frictionally coupled to corresponding structure in the abrading attachment 2. It is contemplated that the arm 6 may also be removably attached to the linkage 5.

Figure 6:
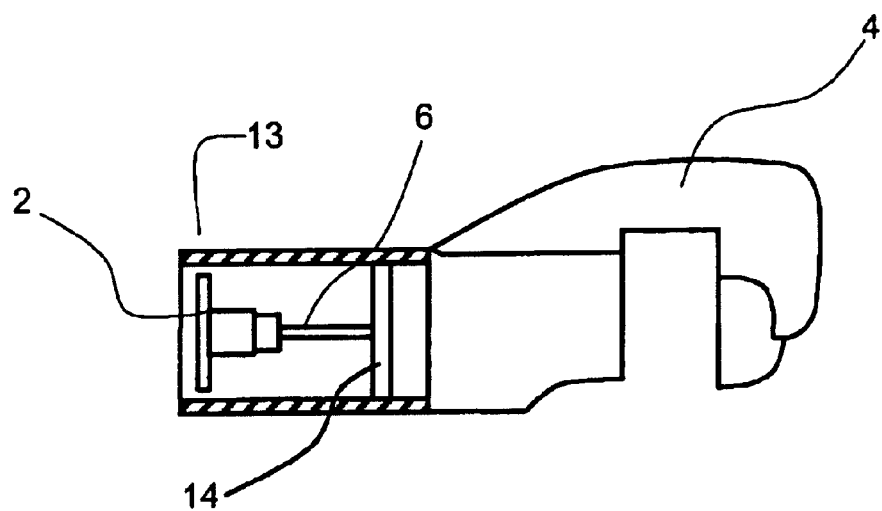
FIG. 6 is a diagram showing a disposable filter disposed within the device.

FIG. 6 is a diagram showing a disposable filter 14 disposed within the tip 13. It is contemplated that materials known in the art may be used to form the filter, and the filter may be removably installed in the device.

As will now be appreciated, the present disclosure provides a microdermabrasion device that may be operated with one hand, and does not require any secondary treatments to be applied. By incorporating a suction channel and forming a partial vacuum within the device as disclosed, the skin may be treated and cleaned in a single operation, allowing the device of this disclosure to be operated with a single hand wherever desired. Disposable filters and abrasive surfaces allow users to maintain effective treatment.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

I claim:

1. A microdermabrasion device comprising:

a body;

a motor housing coupled to said body said motor housing includes a motor;

a partial vacuum housing coupled to said motor housing, said partial vacuum housing comprising a suction channel disposed along an interior surface of said partial vacuum housing;

said motor is coupled to said suction channel for creating a vacuum flow within said suction channel;

an extender arm disposed within said partial vacuum housing, an inner end of said extender arm coupled to said motor housing through an actuating member and a linkage configured to impart an oscillating motion to said extender arm;

a removable tip coupled to said partial vacuum housing, an interior of said tip defining a partial vacuum channel;

an abrading attachment removably attached to an outer end of said extender arm, said abrading attachment being disposed interior of said removable tip and having an abrasive surface disposed on an outer surface; and a terminus of said suction channel being disposed in said partial vacuum channel for drawing skin into intimate contact with said abrasive surface and drawing away removed skin cells.

2. The microdermabrasion device of claim 1, wherein said motor moves said actuating member in a direction traverse to the length of said extender arm, thereby imparting a oscillatory action to the surface of the abrading attachment.

3. The microdermabrasion device of claim 1, wherein said linkage is oscillated about a pivot point.

* * * * *